(12) United States Patent
Caceres et al.

(10) Patent No.: US 9,717,624 B2
(45) Date of Patent: Aug. 1, 2017

(54) APPARATUS AND METHOD FOR PRODUCING COMPRESSES HAVING A COOLING EFFECT

(75) Inventors: Patrick Caceres, Ste Foy les Lyon (FR); Franck Caceres, Ste Foy les Lyon (FR)

(73) Assignee: ALKANTIS SA, Genève (CH)

(*) Notice: Subject to any disclaimer, the term of this patent is extended or adjusted under 35 U.S.C. 154(b) by 1005 days.

(21) Appl. No.: 13/881,159

(22) PCT Filed: Oct. 26, 2011

(86) PCT No.: PCT/IB2011/002567
§ 371 (c)(1),
(2), (4) Date: Apr. 26, 2013

(87) PCT Pub. No.: WO2012/056308
PCT Pub. Date: May 3, 2012

(65) Prior Publication Data
US 2013/0218245 A1    Aug. 22, 2013

(30) Foreign Application Priority Data

Oct. 26, 2010 (FR) .................................. 10 04206
Oct. 26, 2010 (FR) .................................. 10 04207

(51) Int. Cl.
*B65B 9/04*  (2006.01)
*B65B 29/10* (2006.01)
(Continued)

(52) U.S. Cl.
CPC .............. *A61F 7/0241* (2013.01); *A61F 7/02* (2013.01); *A61F 7/10* (2013.01); *B65B 9/04* (2013.01);
(Continued)

(58) Field of Classification Search
CPC .. B65B 9/02; B65B 9/04; B65B 29/00; B65B 29/10; B65B 31/028; A61F 7/0241;
(Continued)

(56) References Cited

U.S. PATENT DOCUMENTS 2,925,719 A * 2/1960 Robbins et al. ........ B65B 29/10
                                                      206/219
2,961,678 A * 11/1960 MacLellan, Jr.
                      et al. ....................... A47L 23/10
                                                      15/104.94
(Continued)

FOREIGN PATENT DOCUMENTS

EP          1 607 074 A1     12/2005
WO    WO 2007035312 A2 *  3/2007  ............... A61F 7/10
WO    WO 2007080970 A1 *  7/2007  .............. A61F 7/032

*Primary Examiner* — Stephen F Gerrity
(74) *Attorney, Agent, or Firm* — Oliff PLC

(57) ABSTRACT

The invention concerns the manufacture of personal care articles consisting of compresses having a cooling effect by swelling with water which are presented individually in vacuum packaging. According to the invention, successive doses of powder comprising absorbent particles are placed in grooves formed by elastic deformation in a lower sheet made of water-permeable textile material, which is continuously unwound, and covered with an upper sheet, which is continuously unwound at the same time as the lower sheet. The lower sheet is then heat-welded in the intervals between adjacent grooves thus isolating the grooves from each other. Successive compartments each containing a dose of the powder are then enclosed in each groove by heat-welding the sheets along transverse weld lines across the width of the moving sheet assembly.

12 Claims, 5 Drawing Sheets

US 9,717,624 B2
Page 2

(51) Int. Cl.
  *B65B 31/02* (2006.01)
  *A61F 7/02* (2006.01)
  *A61F 7/10* (2006.01)
  *A61F 7/00* (2006.01)

(52) U.S. Cl.
  CPC ............ *B65B 29/10* (2013.01); *B65B 31/028* (2013.01); *A61F 7/106* (2013.01); *A61F 2007/0098* (2013.01); *A61F 2007/026* (2013.01); *A61F 2007/0211* (2013.01); *A61F 2007/0214* (2013.01); *A61F 2007/0219* (2013.01); *A61F 2007/0258* (2013.01); *A61F 2007/0276* (2013.01); *Y10T 156/1002* (2015.01); *Y10T 156/1052* (2015.01)

(58) Field of Classification Search
  CPC .............. A61F 7/106; A61F 2007/0098; A61F 2007/0211; A61F 2007/0214; A61F 2007/0258; A61F 2007/026
  USPC ........... 53/450, 453, 546, 553, 559; 156/279
  See application file for complete search history.

(56) References Cited

U.S. PATENT DOCUMENTS

| | | | | |
|---|---|---|---|---|
| 3,072,958 A * | 1/1963 | Collins | B29C 33/52 | 156/279 |
| 3,587,578 A * | 6/1971 | Walker | A61F 7/02 | 604/304 |
| 3,892,060 A * | 7/1975 | Stanley, Jr. | B65B 9/12 | 53/127 |
| 3,940,905 A * | 3/1976 | Perry, 3rd | A61F 7/03 | 53/133.6 |
| 3,965,651 A * | 6/1976 | Reichlin | B65B 9/042 | 53/559 |
| 4,085,560 A * | 4/1978 | McClosky | B29C 65/7894 | 156/290 |
| 4,396,447 A * | 8/1983 | Firth | B29C 53/04 | 156/201 |
| 4,462,224 A * | 7/1984 | Dunshee et al. | A61F 7/106 | 206/219 |
| 4,530,869 A * | 7/1985 | Tesch | A61F 7/02 | 156/250 |
| 4,656,042 A * | 4/1987 | Risler | A23B 7/01 | 220/506 |
| 4,995,217 A * | 2/1991 | Francis, Jr. | A61F 7/03 | 53/410 |
| 5,031,418 A * | 7/1991 | Hirayama et al. | A61F 7/10 | 62/457.2 |
| 5,062,269 A * | 11/1991 | Siegel | A41D 13/0053 | 126/204 |
| 5,161,350 A * | 11/1992 | Nakamura | B65B 9/067 | 53/133.4 |
| 5,313,809 A * | 5/1994 | Isaacson et al. | A61F 7/03 | 156/145 |
| 5,682,726 A * | 11/1997 | Green et al. | A61K 9/7023 | 53/433 |
| 6,127,294 A * | 10/2000 | Koiso et al. | A61F 7/032 | 156/145 |
| 6,524,331 B1 * | 2/2003 | Kohout et al. | A61F 7/02 | 5/421 |
| 6,823,649 B1 * | 11/2004 | Pauchet | B65B 61/02 | 53/133.8 |
| 7,776,290 B2 * | 8/2010 | Michalsky et al. | B65D 81/3266 | 141/11 |
| 7,794,485 B2 * | 9/2010 | Caceres et al. | A61F 7/10 | 607/114 |
| 2002/0020151 A1 * | 2/2002 | DelDuca et al. | B65B 9/073 | 53/474 |
| 2004/0149732 A1 * | 8/2004 | Usui et al. | A61F 7/034 | 219/528 |
| 2005/0283212 A1 | 12/2005 | Caceres et al. | | |
| 2006/0278335 A1 * | 12/2006 | Moriura et al. | A61F 13/15658 | 156/279 |
| 2007/0027415 A1 * | 2/2007 | Kopreski | A61F 7/106 | 602/2 |
| 2007/0267583 A1 * | 11/2007 | Dodo | A61F 7/034 | 250/493.1 |
| 2009/0320411 A1 * | 12/2009 | Carvallo | B65B 29/10 | 53/433 |
| 2011/0214392 A1 * | 9/2011 | Niven | A61J 1/035 | 53/375.9 |

* cited by examiner

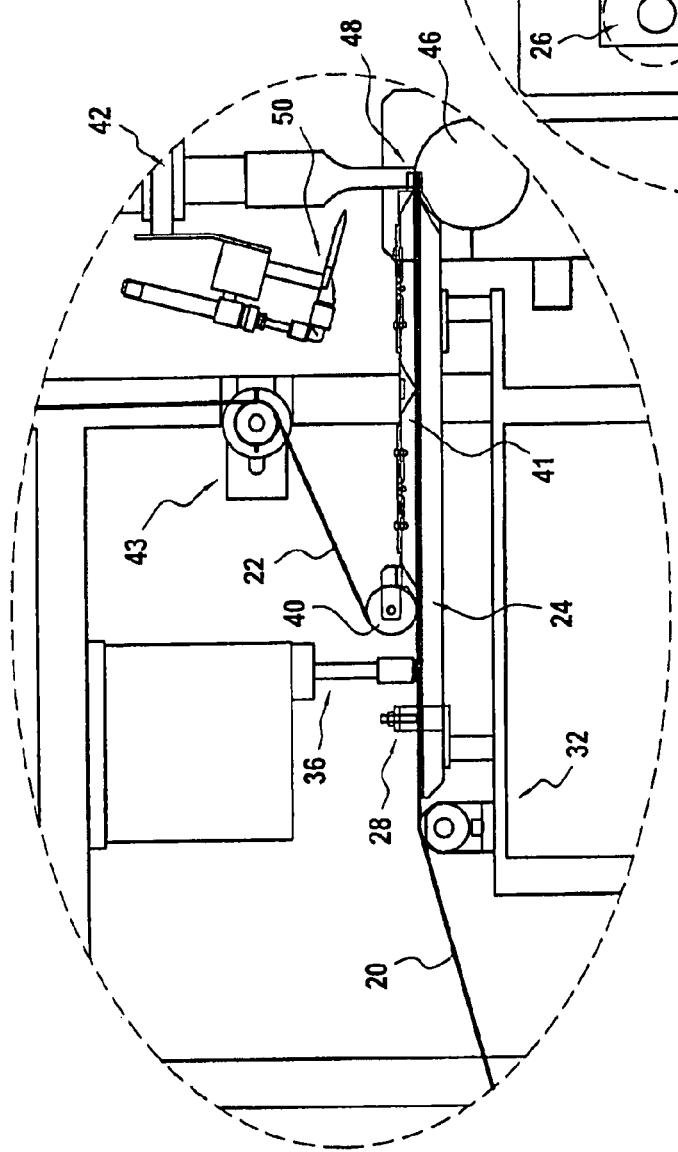
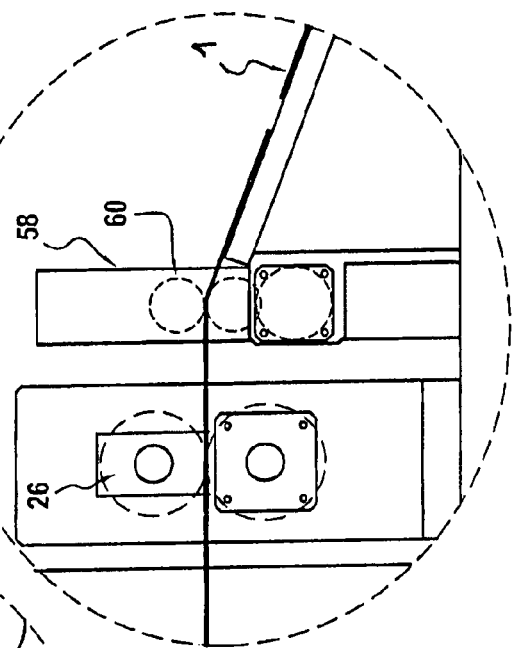

APPARATUS AND METHOD FOR PRODUCING COMPRESSES HAVING A COOLING EFFECT

This invention concerns the industrial manufacture of personal care articles consisting of compresses having a cooling effect by swelling with water.

This type of compress is well-known in the field of medical devices in particular. Operation is based on the potential cryogenic activity of absorbent polymer particles having retained large quantities of water. These are described as active-cooling water-absorbing polymers or polymers activated by swelling with water. The cryogenic effect is mainly due to the vaporization of water during desorption outside the absorbent particles.

The prior art, and particularly European Patent Application n° EP 1 607 074, includes this type of compress based on water-activated absorbing polymers, which are enclosed, in their dry state, in sterile packaging with the activation water in a separate bag, in a personal care article, particularly for medical use, the component parts of which are preserved in their original state in sterile outer packaging up until the water bag is broken and the polymer inside the compress swells up in view of use.

This invention is aimed at large-scale production of the articles thus formed, under conditions compatible with such production, particularly in terms of rapidity, cost and reliability. Likewise, it also proposes to perfect the construction of the articles themselves by making improvements to their properties, particularly with respect to the cooling quality of the compresses and their safe use.

The characteristic features of this invention primarily concern manufacture of the actual compresses, in the form of absorbent polymer in the dry state enclosed in a water-permeable film. Other interesting additional characteristic features concern the assembly of each compress with a breakable water bag in vacuum packaging. It should also be observed that some of the characteristic features of this invention benefit both the article manufacturing process and equipment and the properties of the articles themselves. This is the case in particular for the distinctive characteristic features of the sheets used to enclose the polymer in the compress and the walls of the sterile outer packaging of the finished article with the relative arrangement of the water bag and the compress inside said outer packaging.

Whether in terms of processes or equipment, the invention will mainly comprise the lamination of water-permeable absorbent polymer particles between two sheets of retention material for the large-scale production of so-called dry compresses containing the polymer in dry state distributed among several compartments which together form a flat compress.

For one of the sheets, preferably that used as the lower sheet during manufacture of the compresses, a material having reversible heat deformation should preferably be chosen. In the case of the other sheet, preferably that used as the upper sheet during manufacture, its mechanical strength should be considered, particularly its tensile elongation during lamination, even if this means greater permeability of the corresponding wall in the dry compress obtained. As a result, it is the face of the compress occupied by the heat deformable and more permeable sheet that will be chosen to be placed up against the water bag in the finished article.

Under its preferred embodiments, the invention will also use lamination techniques in a packaging unit carrying out large-scale production of the finished articles for commercialisation, in which each compress is enclosed with its water bag in vacuum packaging. Said packaging is formed from two continuously moving sheets made of watertight, airtight material welded together around each water bag and dry compress assembly. In the preferred embodiments of the invention, the moving lower sheet in the manufacturing process is of the hot plastic deformation type, which means that recesses are formed for the water bags under each compress whereas the mechanical properties of the moving upper sheet must be such that it is completely resistant to deformation. This not only results in good embodiment conditions for the manufacturing process in the packaging unit, but also gives good results for the conditions of use of the finished article. It will be easy for the user to ensure that the water bag breaks and releases water by pressing on the wall of the relatively rigid outer packaging formed by said upper sheet, particularly when it is immediately next to the water bag.

The production of a manufacturing plant according to the invention and the corresponding process will now be defined in reference to the preferred embodiments of the invention, which are not, however, exhaustive.

The plant mainly comprises a manufacturing unit for dry compresses designed to absorb water in order to produce the cooling effect. A lower sheet made of water-permeable material (preferably a textile material) is continuously rolled out flat along the unit to the delivery end after passing under an absorbent-particle powder-feed hopper. Successive doses of said powder are placed in grooves formed longitudinally in said lower sheet by elastically reversible deformation of the sheet. It is then covered with an upper sheet (preferably also made of a water-permeable textile material) which is continuously rolled out flat on top of the lower sheet towards the delivery end of the unit.

Correct distribution of the polymer over the entire surface of each compress is thus ensured during delivery of the sheets, both in the transverse direction of delivery due to the presence of various grooves side by side and in the longitudinal direction of delivery due to the fact that each dose of powder delivered is automatically spread in that direction over a surface area corresponding to that of a compress.

According to another characteristic of the invention, the adjacent grooves filled with powder are isolated transversely from each other by welding the upper and lower sheets together in the intervals between the adjacent grooves, and successive compartments each containing a dose of powder are enclosed in each groove by welding the sheets together along transverse weld lines perpendicular to the direction of delivery.

Thus, immediately after the powder is deposited, the compartments are delimited to ensure that the powder will be correctly and uniformly distributed over the entire surface of each compress. It should be noted here that in the finished compress the grooves become less defined because at the end of the dry compress manufacturing unit, the lower sheet tends to elastically resume its original flat shape.

After welding, the two laminated sheets form the envelope enclosing the absorbent particles. They are thus water permeable. An unwoven textile material is preferably used. In practice, it must be ensured that one of the two sheets is made of water-permeable material while the other can be made of less loosely woven and therefore stronger material. In this case, the more water permeable-sheet is preferably used for the lower sheet because its flexibility makes it more apt to form the groove to take the powder.

According to a characteristic of the invention, the grooves in which the powder is deposited are formed elastically in the lower sheet by individual pins placed in a line perpendicular to the direction of delivery of the lower sheet of the compress, with said pins heating the taut lower sheet and deforming it mechanically and elastically. The sheet is thus temporarily deformed until it tends to regain its original shape after the powder has been deposited. There will be a pin for each groove required.

According to a characteristic of the invention, the powder is deposited by a series of fillers spaced so that each filler is located above one of the grooves in the lower sheet as it moves along. The position of the fillers is such that depositing of the powder is controlled and repeatable so that the same quantity of powder will be present in each compress and each groove.

According to a characteristic of the invention, cooling during the welding operations is provided by blow tubes which are equipped with baffles to protect the powder-filled grooves from blasts of air and thus ensure that the powder is correctly distributed.

Furthermore, the manufacturing plant according to the invention has a packaging unit after the dry compress manufacturing unit.

In this unit, individual thermoplastically-formed receptacles to take the dry compresses are made in a watertight, airtight sheet which is delivered flat to the delivery end of the unit so that a water bag made elsewhere and a dry compress made previously can be deposited on the sheet one on top of the other.

The resulting assembly is then covered with a second watertight, airtight sheet which is delivered flat to the delivery end of the unit at the same time as the lower sheet.

The fact that the two sheets forming the walls of the outer packaging are watertight means that the water released from the bag will be entirely used to impregnate the compress. The fact that the sheets are airtight and that there is a vacuum between the sheets before welding creates an environment that is protected from moisture in the air until the packaging is opened to take out the impregnated compress. If manufacture is carried out under sterile conditions, the watertightness and airtightness of the sheets and the vacuum packaging will ensure that sterile conditions are maintained until the packaging is opened.

According to a characteristic of the invention, construction of the receptacles by thermoplastic forming is such that a dry compress and a corresponding water bag are completely contained in the volume of said receptacle.

It must be ensured that the compress and the bag can no longer move once they are placed in the receptacle and that the water bag inside the receptacle is protected so that it cannot break unintentionally.

A system can be provided to ensure that the water bag is kept in a central position with respect to the compress in the vacuum packaging.

The water bags can also be made in the manufacturing plant, preferably in a unit alongside the dry compress manufacturing unit.

In the water bag manufacturing unit, which is placed before the packaging unit, the two edges of a plastic sheet are brought together and welded along a generatrix to form a closed tube. The weld along the two edges is designed to ensure that the bag will remain watertight throughout the manufacturing process and during handling of the bags and that, in the finished product, it will break when the article, and therefore the water bag, are pressed flat so that the water impregnates the compress. A frangible zone is thus defined which is designed to give way when the user wants to impregnate the dry compress with water in order to activate the cooling effect on a wound.

After the edges have been welded together, the resulting tube is placed in thermoplastic welding jaws perpendicular to the axis of the tube and the tube is welded transversely to form the lower weld line of the bag. Pressurised water is then fed in successive doses into the centre of the tube to fill it with water. The water level in the tube is then checked using a water level probe and an upper transverse weld carried out, thus forming a bag enclosing the water. The upper weld line must be located sufficiently below the upper water level in the bag formed by the two sheets to evacuate any surplus water during welding. It must be checked that no air bubbles have been trapped in the bag and that the amount of water in the bag is the required quantity for correct impregnation of the compress. In continuous water bag production, the resulting bag is cut off and removed from the manufacturing unit so that it can be placed in the outer packaging. The upper weld line of the previous bag then forms the lower weld line of the next bag and the filling, welding and cutting process is continued cyclically.

According to a characteristic of the invention, each dry compress made by the dry compress manufacturing unit and each water bag at the delivery end of the manufacturing unit is transferred such that a water bag and a compress are transferred to a preformed receptacle in the outer packaging in the packaging unit.

The transfer step also includes a videometric inspection operation to ensure that there is a dose of absorbent powder inside each compress.

The invention will now be completely described in relation to its preferred characteristic features and their advantages, referring to the following figures:

FIGS. 4 and 5 are enlargements of areas IV and V on FIG. 3;

Figure 1:
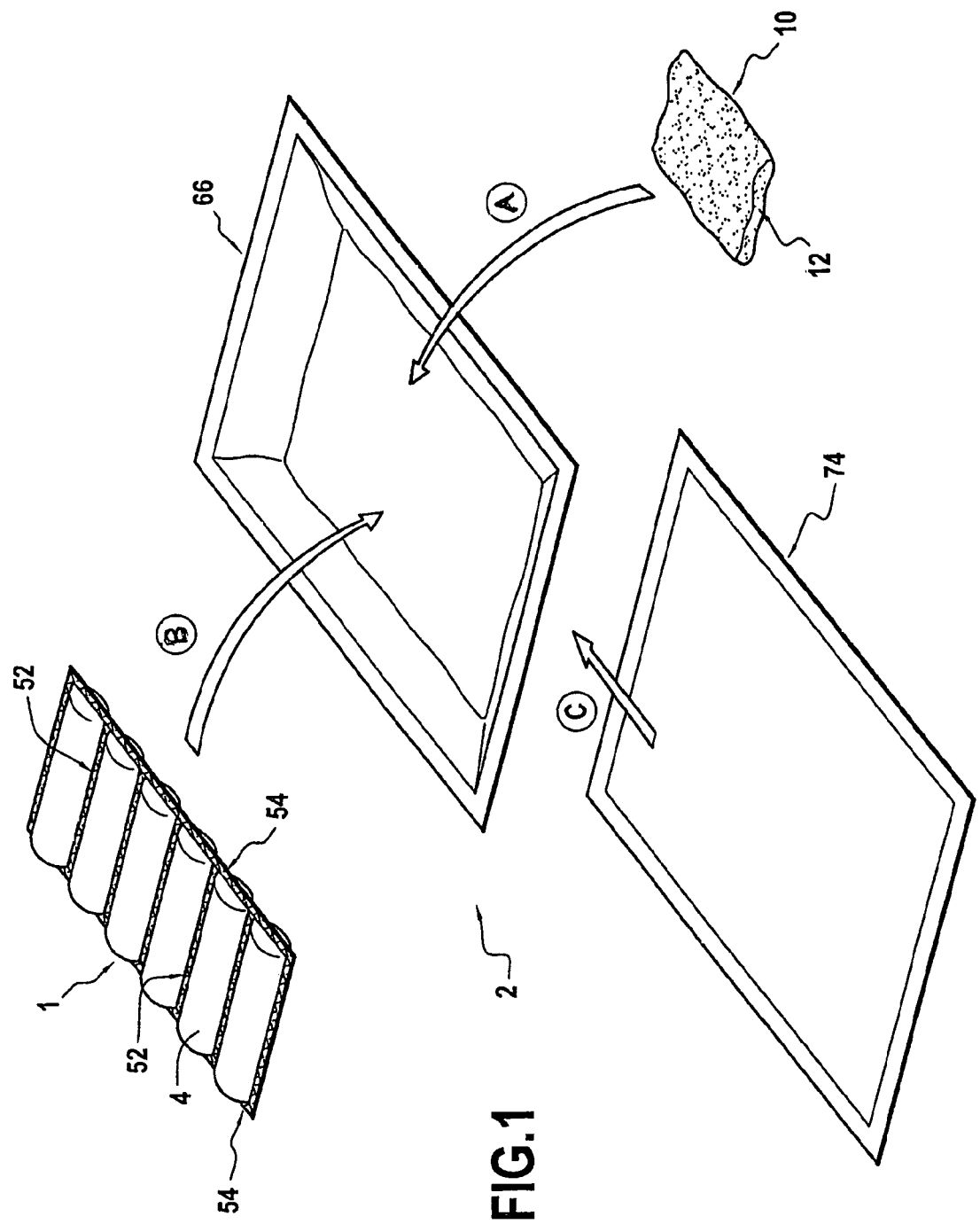
FIG. 1 represents an article having a cooling effect according to the invention, in an exploded view showing the two sheets forming the outer packaging and a compress and water bag which are designed to be lodged together between the two sheets in the finished product.

The dry compress 1 according to the invention is presented as an integral part of article 2, as illustrated by an exploded view in FIG. 1 for better comprehension.

An article such as that described previously is made in the following way, referring to FIGS. 2 to 7 in particular.

A dry compress is prepared, for example, in the form of compartments 4 each with an adequate amount of dry polymer particles 6, in a compress manufacturing unit 8 described below.

A water bag 10 is prepared independently, in a water bag manufacturing unit, making sure there is a frangible area 12 on the surface, particularly along a weld line.

A compress and a water bag are then deposited in the article packaging unit 14 in which the upper and lower sheets of the outer packaging are welded together to enclose the compress and bag in the packaging.

The article 2 is then sterilised using beta or gamma ray treatment. The inside of the outer packaging, including the compress and water in the bag, is thus made sterile. None of the bag components are damaged, except for a small number of the particles whose cross-linking is destroyed. However, a sufficient number of active particles still remains to ensure the effective delivery of cold.

The manufacturing process according to the invention and the manufacturing installation required to implement the process will now be described, referring in particular to the manufacturing plant which has two lamination units in the same facility, that is, a dry compress manufacturing unit 8 and a finished product (compress) packaging unit 14, with a conveyor belt 16 and grippers 18 to transfer the dry compresses from one unit to the other.

The dry compresses manufactured as above, together with the water bags, are designed to feed the packaging unit. They are collected at the delivery end of the dry compress manufacturing unit and are deposited on the packaging unit from the side, where a film has already been pre-formed to make the receptacles for the compresses and water bags.

The dry compress manufacturing unit 8 has two rolls to continuously deliver the water-permeable textile sheets 20, 22, which are then welded together in the manufacturing plant after the absorbent powder 6 has been injected between the sheets. A cutting unit divides the bands into dry compresses after welding.

A first roll of textile film 21 designed to form the lower sheet of the compress 20, is continuously unrolled. The film is then transferred by guide rollers until it reaches a conveyor belt 24 (visible in FIG. 3). The film is then conveyed by drive rollers 26 to the end of the unit, as described below.

Pre-forming pins 28 are placed above the belt, along the path of the lower sheet. They project beyond the delivery plane of the lower sheet and create a temporary elastic deformation of the lower sheet in the form of longitudinal grooves 29. The textile material is heat-deformed by the pins which heat up and form continuous grooves along the moving lower sheet. The pins are supported by an arm 30 (FIG. 7), fixed to the frame of the unit 32, which passes above and on either side of the moving lower sheet and conveyor belt. The lower sheet is mechanically deformed downwards to form grooves by elastic deformation which subsequently form powder retention compartments during manufacture of the dry compress.

A powder deposit device 34, located immediately after the pre-forming pins in the direction of delivery of the sheet, consists of a filler support 36 mounted at the delivery end of an absorbent-particle powder-feed hopper 38. The fillers are spaced so that each filler 36 is located above a groove previously formed in the moving sheet.

The distributor is of the rotating cylinder type on the surface of which are recesses which feed the powder to the fillers. If the manufacturing unit travels from left to right, as illustrated in the figures, an excess particle exhaust hood, not depicted here, is placed on the left of the rotating distribution cylinder.

Periodically, at the rate at which the compresses to be separated from each other are produced, each filler 36 delivers a predetermined dose of absorbent powder 6 into each groove 29.

The powder is thus deposited in each groove, in successive doses, along part of the length only so that the grooves can be closed by welding perpendicular to the direction of travel and the successive compresses between two transverse weld lines can be cut apart.

The number of pins and fillers corresponds to the number of powder compartments required for a given compress. In the example depicted, there are six pins and six fillers for six grooves, as can be seen clearly in FIG. 7.

Immediately after the powder depositing device, the band of textile material, which is also water-permeable and forms the upper sheet 22 of the compress, is flattened onto the lower sheet 20, so that the previously deposited powder is confined between the sheets. Because the powder has been deposited in the grooves, it is not dispersed when the upper sheet is flattened onto the lower sheet.

The upper sheet is delivered from a second roll 23. The second roll can be fixed to the frame of the unit next to the intersection of the two sheets. However, as illustrated in the figures, it is preferable for the two rolls to be placed near each other. This means there is only one fabric loading area and, when the unit is so designed, a single lapping area where the sheet at the end of one roll is joined end-to-end with the sheet at the beginning of the next roll.

As a result, the distance travelled by the upper sheet is longer since it has to pass above the fillers 36 so as not to interfere with the powder feed as the powder must be placed between the upper and lower sheets of the compress.

The upper sheet is flattened against the lower sheet and the powder deposited in the grooves of the lower sheet by a flattening roller 40 which feeds the upper sheet and under which passes the lower sheet. Here, the lower sheet 20 is supported by the conveyor belt 24 which starts before the pre-forming pins and ends at the first welding unit 42 that welds the two sheets together. As described below, the conveyor belt is designed to pass underneath a welding table 41 where the sheets with the powder inside are compressed between the belt and said table.

Guide rollers are provided along the path of both the upper and lower sheets. Here in particular, is to be found roll 43 placed before flattening roller 40 along the path of the upper sheet, and mounted according to a floating axis which is not parallel to the axis of rotation of the other rollers in order to facilitate transverse adjustment of the upper sheet so that its edges correspond to those of the lower sheet.

The assembly formed by the upper and lower sheets enclosing the powder travels along the conveyor belt and under the welding table which is mounted directly on the frame after the flattening roller and holds the assembly in place while flattening it, thus ensuring that the powder is dispersed inside the grooves. The welding table has teeth 44, mounted across the path of the sheets in the intervals between grooves where there is no powder. In the intervals between the grooves, said teeth, series-mounted in the longitudinal direction, are designed to keep the upper sheet firmly flattened against the lower sheet which is pressed up against the conveyor belt This means that the powder is kept inside the grooves underneath the welding table while the assembly is being flattened and the grooves are being made deeper, thus preventing powder from being found in the intervals between the grooves when the assembly reaches the ultrasound welding units, since the intervals correspond to the future longitudinal weld lines between the grooves and must therefore remain free of powder for optimised welding.

At the end of the welding table, the assembly leaves the conveyor belt and is transferred to the first ultrasound welding unit 42 which has a block anvil 46 and a set of sonotrodes 48 (FIGS. 4 et 6). The block consists of a roller around which are wound seven bands each forming a raised area 47 corresponding to each of the five intervals between the grooves and the two side edges. This results in seven sonotrodes which apply pressure to the sheets at each of the seven bands and restore the energy produced by the ultrasounds in order to spot weld the upper sheet to the lower sheet longitudinally in the direction of travel of the band.

Figure 6:
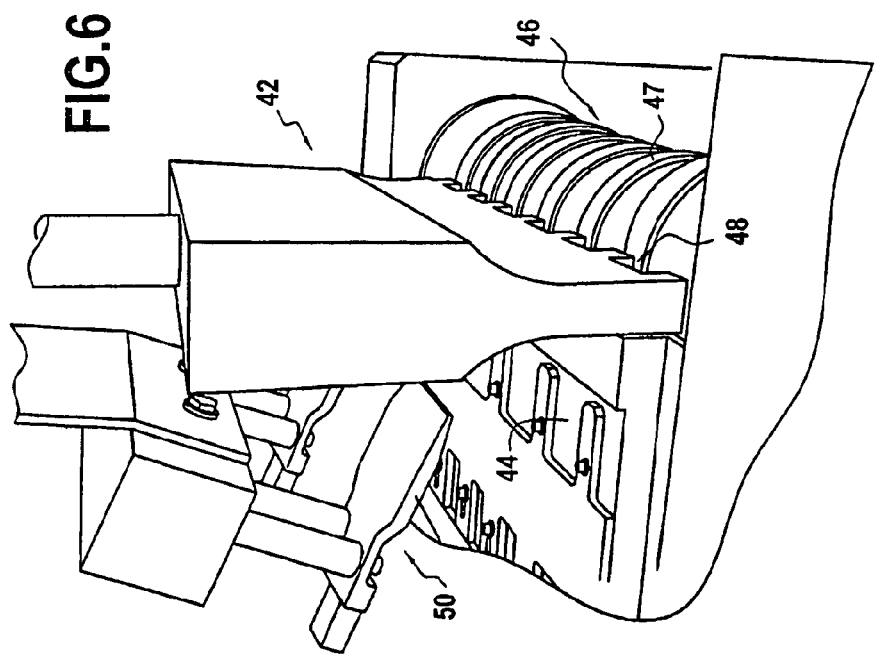
FIG. 6 represents an enlargement of the first welding unit in the compress manufacturing unit in FIG. 3, operating unloaded without sheets.

The first welding unit also has blow tubes 50, as illustrated in the figures, especially FIGS. 4 and 6.

The moving band now consists of the two sheets of permeable non-woven material enclosing small amounts of super absorbent particle powder distributed and retained in the cavities formed by the grooves which are now isolated by longitudinal weld lines 52. Transverse weld lines 54 are now produced in each groove perpendicular to the direction of travel in order to separate successive sections of film and powder designed to form successive dry compresses.

To do this, the band passes through a second ultrasound welding unit 56 which consists of a sonotrode and helical-shaped block on a rotating cylinder. The block has a raised surface over a width corresponding to twice the length of a line across the end of a compress, with the weld being carried out before cutting. A sonotrode applies pressure to the sheets forming the moving band and restores the energy produced by the ultrasound to weld the upper sheet to the lower sheet transversely.

Like the first welding unit, the second welding unit has a cooling device for the cylinder block. Ideally, the cooling device should have a curved baffle plate onto which air from the blow tubes is directed. This prevents air from being blown directly onto areas containing powder particles which otherwise would be displaced to welding areas.

Displacement of the moving band, now composed of successive dry compresses still attached to each other transversely, with each compress taking up the width of the moving band, continues via a mechanism consisting of two drive rollers 26 which turn in opposite directions and pinch the successive compresses between them. The drive rollers provide the traction required to pull the band through the different parts of the manufacturing unit placed upstream. The movement given to the band transfers it to the cutter 58 located downstream of the drive rollers.

The cutter consists of two rollers through which the successive dry compresses pass. One of the rollers has a sharp blade 60 placed helically which cuts the assembly transversely each time the other roller is located opposite. The rotational speed and diameter of the roller with the sharp blade are such that the blade cuts the moving assembly transversely in the middle of each transverse end weld, thus separating each dry compress from the others.

Cut dry compress 1 is placed at the delivery end of manufacturing unit 8 on conveyor belt 16.

Figure 2:
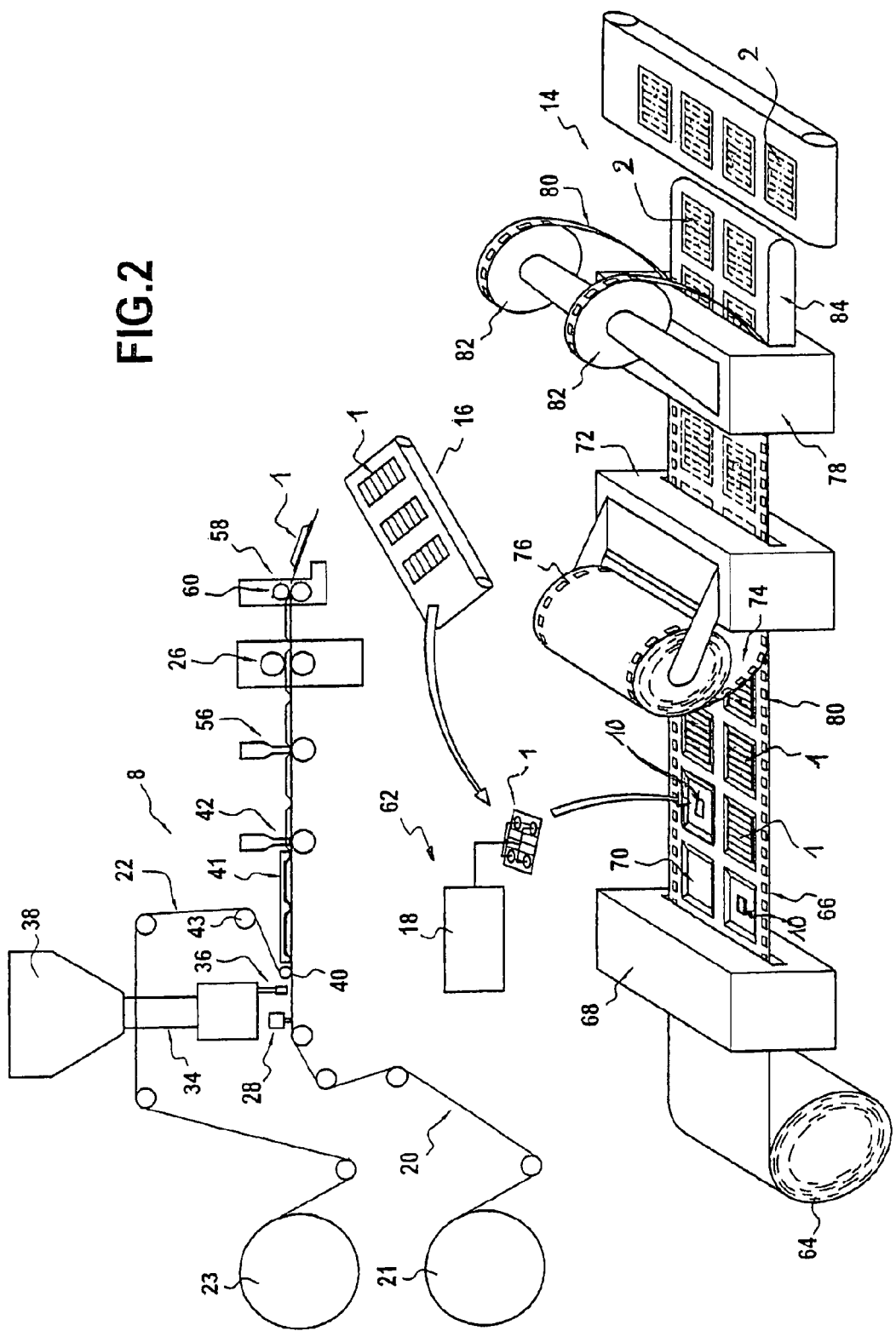
FIG. 2 represents a general view of the article manufacturing installation represented in FIG. 1, with a large-scale dry compress manufacturing unit, a transfer system and a vacuum-packing unit for each compress assembled with a water bag.
Figure 3:
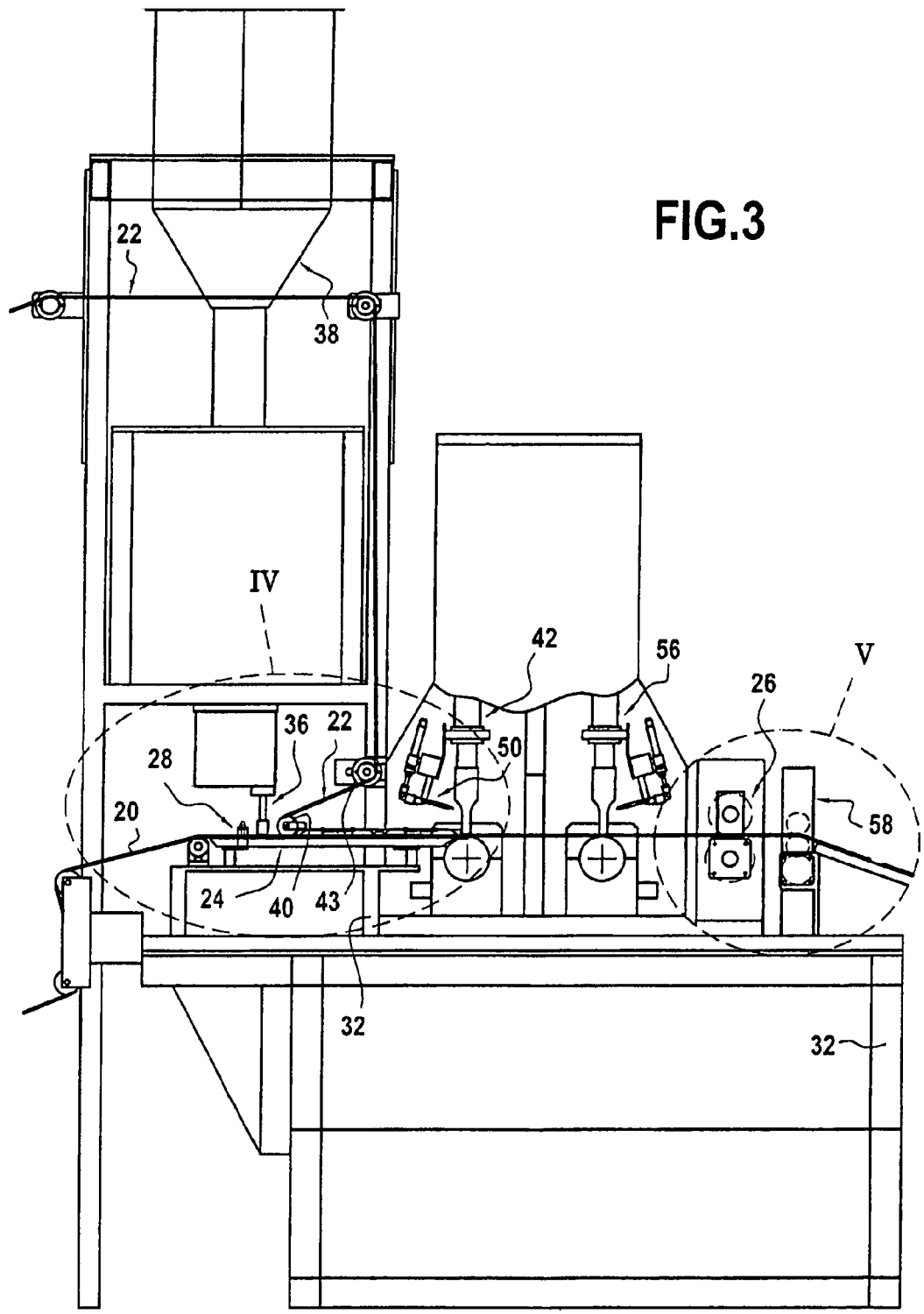
FIG. 3 represents a partial view of the manufacturing unit illustrated in FIG. 2, without the rolls of unwoven film.
Figure 7:
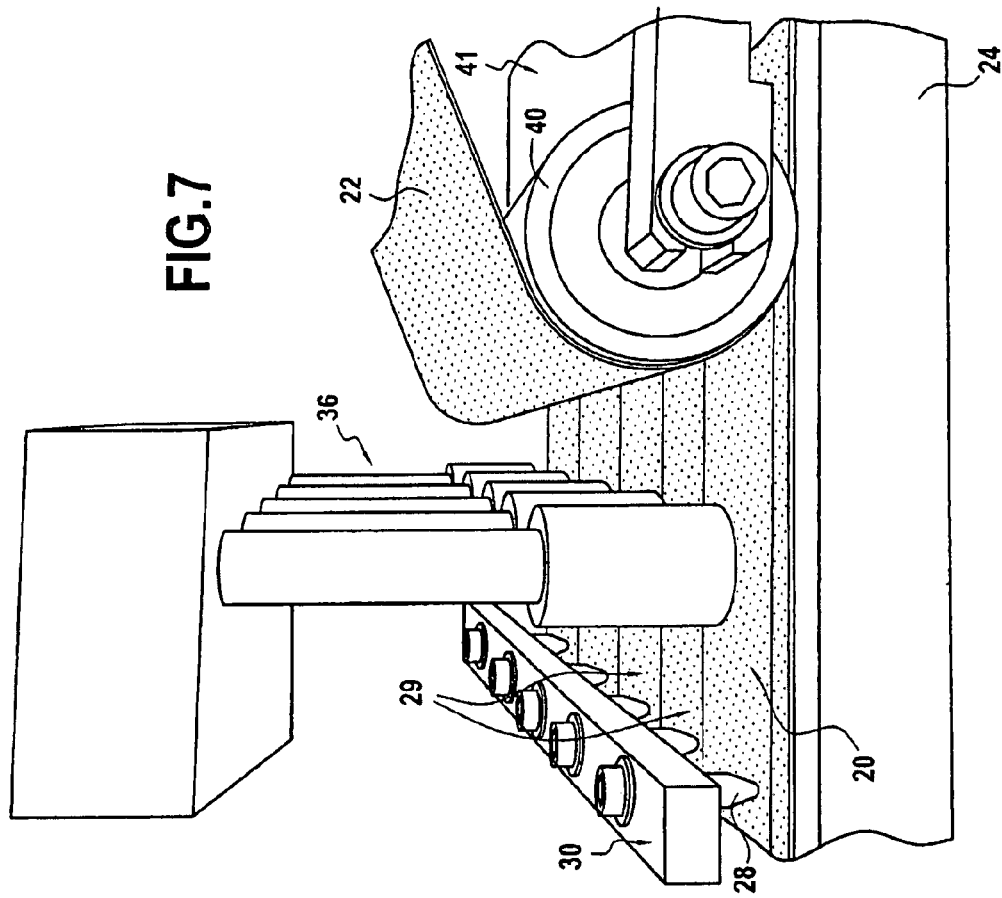
FIG. 7 represents an enlargement of the absorbent powder depositing unit in the compress manufacturing unit in FIG. 3, with the unwoven lower sheet heat-deformation system upstream and the unwoven upper sheet feed downstream.

As illustrated in FIG. 2, the installation has a pneumatic gripper transfer device 62 which is designed to automatically pick up a pile of dry compresses from the conveyor belt, transfer them from said compress manufacturing unit to the packaging unit, release them by deactivation of the suction caps and place them in their respective locations, that is, as described below, on the lower outer packaging sheet of the article, which has already been pre-formed.

Each gripper 81 of transfer device 62 has a suction cup and a means of connecting the suction cup to a vacuum circuit. Each of the grippers is thus able to pick up a dry compress by means of suction and release it by blowing air into said suction cup. The grippers are grouped together in modules forming a master gripper. The suction cups of the different grippers form a two-dimensional mesh of predetermined surface area.

Preferably, transfer device 62 is designed to simultaneously pick up several compresses from the conveyor belt, in this case two, and place them at the same time in receptacles formed side by side in the packaging unit. It is essential, in relation to the transfer operation according to the invention, that the dry compresses and associated water bags are placed in the corresponding receptacle before being covered by the upper sheet and vacuum packed.

The transfer device can be associated with an inspection post which uses videometry to ensure that the dry compress contains absorbent powder, before it is placed in the sterile article.

As indicated above, the manufacturing plant according to the invention described here also has a vacuum-packing unit for finished articles 14 which includes a lamination phase. Two rolls deliver impermeable plastic films which are heat-bonded to each other to form the outer packaging after a compress and a water bag have been placed between the two films in a receptacle pre-formed in one of the films, and after creation of a vacuum.

A first roll 64 of watertight, airtight film is paid out so as to form the lower sheet of article 66, which continuously feeds the vacuum-packing unit.

The lower sheet passes into an oven 68 in which certain areas of the sheet are heat-treated to form receptacles 70. Here, two receptacles are formed side by side on the same width.

In the construction method depicted, the lower sheet is kept taut between two series of pincers which grip the edges and are supported by two lateral drive chains such that a counter-mould is not required for pre-forming.

The lateral drive chains deliver the lower sheet non-continuously, followed by the upper sheet, as described below. The non-continuous delivery, which is different from the continuous delivery in the dry compress manufacturing unit, ensures that the lower sheet remains a sufficiently long time in the oven for the receptacles to be formed, and for the vacuuming and heat welding operations described below to be carried out.

After leaving the forming oven, each receptacle 70 is filled with one dry compress and one water bag 10. It should be observed here that the compresses and water bags reach the packaging unit 14 from the side and not at the feed end of the unit. A dry compress and a water bag must be lodged in a receptacle already pre-formed in the lower sheet of the outer packaging before being covered with the upper sheet of the outer packaging. It can therefore be seen that the thickness of the compresses at the delivery end of the manufacturing unit must be such so that a dry compress and its water bag will be entirely contained in the volume of the receptacle.

The dry compresses are transferred by grippers 18. The water bags can also be transferred in the same way, unless they are transferred manually. As described below as a variant, the position of the water bag with respect to the compress in the article can be different from that depicted in FIGS. 1 and 2, in which the water bag is placed first on the lower sheet of the outer packaging (as shown by arrow A in FIG. 1), with the compress placed on top of the water bag so that it is between the compress and the lower sheet of the outer packaging.

In this construction, the compress is placed on top of the water bag (arrow B, FIG. 1) and held in position by the upper sheet (arrow C, FIG. 1). The water bag is initially placed in the middle of the receptacle and the compress is placed on top without changing the central position of the water bag. An adhesive can be placed on the water bag so that it will maintain its central position which is the preferable position for uniform water dispersion in the compress.

It should be observed that it is more effective to place the water bag against the lower sheet of the compress when said lower sheet is more permeable to water than the upper sheet of the compress.

The lower sheet of the outer packaging, with the dry compress and its water bag placed in the receptacle, then enters a heat welding and vacuum unit 72. Prior to this, an upper sheet 74 is placed on top of the lower sheet. For this purpose a roll of film 76 is fixed above the heat welding unit and continuously unwound.

The upper sheet is also kept taut between two series of pincers which grab the edges and are supported by two lateral drive chains. The tension within the same set of pincers enables the upper sheet to be adjusted transversely with respect to the lower sheet so that the sheets are kept sufficiently taut for the welding and vacuum operations to be carried out without shrinkage.

The welding and vacuum operations in unit 72 are carried out in three steps. First the edges around each receptacle are closed by welding the sheets together except for the rear edge of the receptacle. A vacuum is then created in the direction of travel of the assembly, before transverse welding of the rear edge of each receptacle. Each receptacle is then completely closed by welding the rear edge which was initially kept open so that the vacuum could be created. The heat welding operation therefore includes all the areas around the compress receptacles. The heat welding unit thus ensures that the upper sheet is bonded to the lower sheet, effectively enclosing the compress and water bag inside, in an airtight vacuum.

The materials used for the sheets in the outer packaging differ according to whether the upper or lower sheet is used to produce the receptacles by heat forming. For example, if the receptacle is to be formed in the lower sheet it must be made of a thermosetting material whereas the upper sheet can be made of another type of plastic. However, both sheets must be watertight, principally to keep the water inside the outer packaging when the water bag is broken. They must also be airtight so that the assembly will remain in a vacuum and preserve its sterile state during treatment operations and be protected from the intrusion of bacteria at ambient temperature. The two sheets are heat-welded together on opposite sides to ensure airtightness and watertightness and vacuum packing. One of the joins, preferably the rear edge weld produced after vacuum packing, must have a low level of resistance to ensure peelability so that the finished medical device can be manually opened in view of using the cooled, water-impregnated compress contained within. Peelability is facilitated by using a slightly adhesive material for at least one of the two sheets in the outer packaging.

As described above, the lateral drive chains ensure that the two sheets move forward non-continuously to ensure the necessary pause for the assembly to remain for long enough in the welding and vacuuming unit for a vacuum to be created and the sheets to be welded together.

On leaving the unit, the edges of the sheets that have been welded together are grabbed by pincers on chain conveyors as above, to ensure the same discontinuous travel.

The assembly then passes into a cutting station 78 in which the individually packaged compresses are cut with a punch, longitudinally and transversely to separate the articles from each other. They are also cut off along the sides. The side edges of the films 80 are then wound around reels 82 fixed to the delivery end of the cutting station on either side of the belt and take the sheets through the packaging unit by winding the edges.

As they are cut, the articles in their outer packaging fall away. They can either fall directly into a bin or onto a delivery belt 84 which begins in the cutting station.

The articles are then packed vertically side by side in boxes to prevent premature opening of the water bags which could occur if the articles were stacked flat horizontally one on top of the other.

As described above, the water bags placed in the receptacles with the dry compresses can be taken manually or transferred via a transfer device similar to that described above from a water bag manufacturing machine which can preferably be included in the manufacturing plant according to the invention.

The machine is of the same type as those used for the manufacture of any type of liquid-containing packs. A plastic sheet is folded so that the two side edges are superimposed to form a tube closed by welding along a generatrix. The side weld is such that a frangible area is formed that gives way when the user presses firmly on the article to impregnate the dry compress and thus activate its cooling effect on a wound.

After the edges have been welded together, the resulting tube is placed in thermoplastic welding jaws perpendicular to the axis of the tube and the tube is welded transversely to form the lower weld line of the bag. Pressurised water is then fed in successive doses into the centre of the tube to fill it with water while checking the filling level with a probe. The water is filtered through a 0.2 micron sieve. Chlorine is added for the purposes of antibacterial treatment to prevent contamination of the water as it flows through the pipes. When the water level reaches a predetermined threshold, the bag is welded across the top so that the water is enclosed in the bag. The upper weld line must be located sufficiently below the upper water level in the bag formed by the two sheets to evacuate any surplus water during welding. It must be checked that no air bubbles have been trapped in the bag and that the amount of water in the bag is the required quantity for correct subsequent impregnation of the compress. It should be noted that if a small air bubble is nevertheless enclosed in the liquid, it will necessarily be evacuated during vacuum packing of the assembly formed by the outer packaging, the compress and the bag, since the walls of the bag are made of polyethylene-based polymer and consequently permeable to air.

In continuous water bag production, the resulting bag is cut off and removed from the installation so that it can be placed in the outer packaging. The upper weld line of the previous bag then forms the lower weld line of the next bag and the filling, welding and cutting process is continued cyclically.

The sides are welded in such as way as to ensure watertight closure of the bag and resistance to handling throughout the manufacturing operations on the one hand and breaking of the bag in the finished product on the other hand, as soon as pressure is applied to the article when flat, and therefore to the water bag, so that the compress is impregnated with water.

Variants in the manufacturing plant that are not depicted and use different methods for holding the water bag in position with respect to the compress will now be described.

In a first variant, the water bag is placed at the bottom of the receptacle before the dry compress, as described above, and the receptacle itself has a pre-formed recess at the bottom, in the middle, having the same shape as the water bag. The water bag is slipped into said recess and prevented from moving in both directions. Once the dry compress is placed in the receptacle over the bag, it can no longer move. Since the recess is in the middle of the receptacle, the water bag takes up a central position with respect to the dry compress which will not move when the upper sheet is placed on top of the lower sheet of the outer packaging. Once again, the outer packaging must be large enough to contain the dry compress and water bag placed flat one on top of the other.

In a second variant, it is the compress which is placed at the bottom of the receptacle first and the water bag is placed on top of the compress, in the middle. In this case, the dry compress can be turned upside down when it is being transferred by the grippers and the dry compress placed in the outer packaging first with the lower sheet turned upwards, ready to take the water bag. Thus the water bag is in direct contact with the lower sheet and the water which is expelled from the bag comes into contact with the superabsorbent particles more rapidly. The water bag is kept in the central position by immediate covering with the upper sheet which holds the bag in place with respect to the compress.

In both cases, as in the construction method described above, it is ensured that the water bag is correctly positioned with respect to the dry compress for the best distribution of the water when the bag is forced open.

The result of this manufacturing process is a compress which is easy to use and meets the stringent criteria of sterility in a hospital environment.

The article consists of vacuum-packed outer packaging comprising two sheets 66, 74 welded together, containing a water-filled watertight bag 10 having a frangible area 12, and a compress enclosing polymer particles in the dry state 6. The outer packaging consists of an airtight, watertight material such that the water bag and compress remain sterile when vacuum-packed.

The sheets forming the wall of the outer packaging consist, for example, of a mixture of polyamide and polyethylene. This type of material has the particularity of being compatible with gamma ray sterilisation which means that the material is not altered during sterilisation and that it lets gamma rays through, resulting in effective sterilisation of the elements inside the outer packaging.

The walls of the outer packaging are preferably transparent so that the contents are visible and the condition of the elements inside the outer packaging can be monitored.

The compress and water-filled bag are arranged inside the outer packaging

The compress consists of two sheets welded together and enclosing polymer particles with a high water-absorption capacity, initially in the dry state.

The sheets which enclose the particles consist of nonwoven material that is permeable to air and water. This material is compatible with gamma ray sterilisation, which means that it can withstand sterilisation and does not prevent gamma rays from passing through, thus allowing sterilisation of the particles inside the compress.

Moreover, the material composing the sheets has good resistance to both the pressure exerted by the ambient air on the vacuum-packed article before activation of the polymer and that exerted on the walls of the compress by the polymer particles when they swell rapidly and extensively as a result of the absorption of water. Furthermore, the sheets will have greater water permeability to activate the polymer having a cooling effect if they are made of a material that does not absorb water. For this purpose, an artificial resin fibre, such as polyester resin, is used.

On the edges formed by the opposite ends of each wall, the compress is welded in order to prevent the particles from escaping. The weld lines are relatively wide, between 3 and 7 mm, which increases the resistance of the walls to the force exerted by the polymer particles which dilate when they absorb water.

The sheets forming the compress are bonded together along different longitudinal lines produced by ultrasound welding so as to form several elongated compartments in which the polymer particles are uniformly distributed. In the construction example shown in the figures and especially visible in FIG. 1, the compress has six compartments isolated from each other with respect to the polymer particles. The weld lines obtained are also mechanically resistant to the forces exerted by the polymer particles which swell when they absorb water.

The absorbent polymer particles selected here are also known to be non-toxic. The polymer particles, which are responsible for the cooling effect produced by the compress when the particles which have been previously activated, that is, swollen by the water absorbed, after possibly having remained in a cold environment, produce cold by desorption and vaporisation of the water absorbed.

The water bag is hermetically sealed, by welding in particular. The welds are sufficiently resistant not to give way when the article is handled during transport. However, at least one of the welds is designed to give way, at least partly, when pressure is exerted by the user on the outside surface of the water bag, through the outer packaging. Thus, when the user wants the water contained in the water bag to spread outside the bag, fairly strong manual pressure is exerted on the compress to break the frangible area of the bag and release the water so that it spills into the outer packaging and impregnates the polymer inside the compress.

The water bag contains an adequate amount of water only, without air bubbles insofar as possible. The amount of water is determined by the quantity of polymer particles in the different compartments enclosing the polymer powder and by the water absorption capacity of the particles, such that it is completely absorbed when the water bag is opened. It is doubly preferable that the quantity of polymer should be in excess with respect to the water, first to prevent any liquid water remaining in the outer packaging when it is opened and second so that the particles next to the textile walls of the compress still require water.

The invention claimed is:

1. A plant for manufacturing compresses having a cooling effect, comprising at least a main dry compress manufacturing unit comprising:
 a device for longitudinally moving a water-permeable textile lower sheet which is continuously unwound and delivered flat to a delivery end of said unit, underneath an absorbent particle powder feed hopper;
 a device for depositing successive doses of said powder in grooves formed longitudinally in said moving lower sheet by reversible heat deformation;
 a device for covering the moving lower sheet and powder with an upper sheet which is continuously unwound and delivered flat at the same time as said lower sheet to said delivery end of said unit to form an assembly;
 a device for isolating adjacent powder-filled grooves from each other transversely by longitudinally welding said upper sheet and lower sheet together along intervals between said adjacent grooves;
 a device for forming successive compartments in each groove, each containing a dose of said absorbent particle powder, by welding said sheets together along transverse weld lines across the width of the moving assembly; and a device for cutting the resulting moving assembly into successive dry compresses by moving the assembly between rollers, one of which has a blade, thereby producing successive dry compresses, each containing doses of absorbent particles enclosed tight in separate grooves.

2. The plant according to claim 1, wherein said grooves are formed in said lower sheet by pre-forming pins aligned perpendicular to the longitudinal direction of movement of the lower sheet, with said pins heating the taut lower sheet and deforming the lower sheet mechanically by elastically reversible deformation.

3. The plant according to claim 1, wherein said powder is deposited by a set of fillers spaced so that each filler is located above one of said grooves in the moving lower sheet.

4. The plant according to claim 1, wherein cooling means comprising blow tubes are used to cool the welding areas, with said cooling means being equipped with baffles to protect said powder-filled grooves from blasts of air.

5. A manufacturing plant for vacuum-packed compresses having a cooling effect, comprising a vacuum-packing unit and a dry compress manufacturing unit, said dry compress manufacturing unit comprising:
a device for longitudinally moving a water-permeable textile lower sheet which is continuously unwound and delivered flat to a delivery end of said dry compress manufacturing unit, underneath an absorbent particle powder feed hopper;
a device for depositing successive doses of said powder in grooves formed longitudinally in said moving lower sheet by reversible heat deformation;
a device for covering the moving lower sheet and the powder with an upper sheet which is continuously unwound and delivered flat at the same time as said lower sheet to said delivery end of said dry compress manufacturing unit to form an assembly;
a device for isolating adjacent powder-filled grooves from each other transversely by longitudinally welding said upper sheet and lower sheet together along intervals between said adjacent grooves;
a device for forming successive compartments in each groove, each containing a dose of said absorbent particle powder, by welding said sheets together along transverse weld lines across the width of the moving assembly; and
a device for cutting the resulting moving assembly into successive dry compresses by moving the assembly between rollers, one of which has a blade, thereby producing successive dry compresses, each containing doses of absorbent particles enclosed tight in separate grooves; and said vacuum-packing unit comprising:
a device for thermoplastically forming individual receptacles in a watertight, airtight sheet which is delivered flat to said delivery end of said vacuum-packing unit;
a device for depositing a water bag manufactured by a water bag manufacturing unit and a dry compress manufactured by the dry compress manufacturing unit in each receptacle, one on top of the other;
a device for covering the sheet of formed receptacles each filled with a water bag and a dry compress with a second watertight, airtight sheet which is delivered flat at the same time as said first watertight, airtight sheet to said delivery end of the vacuum-packing unit;
a device for closing edges around each filled receptacle by welding said first and second watertight, airtight sheets together, except for a rear edge of each said receptacle;
a device for successively creating a vacuum within each filled receptacle before transverse welding of the rear edge of each receptacle and complete closure of each receptacle by welding of said rear edge; and
a device for cutting the filled and completely closed receptacles with a punch to obtain individual vacuum-packed compresses having a cooling effect.

6. The manufacturing plant according to claim 5, wherein a volume of each said receptacle is sized such that a dry compress and a water bag are completely contained in the volume of each said receptacle.

7. The manufacturing plant according to claim 5, further comprising means to hold the water bag in a central position with respect to the dry compress in the receptacle.

8. A manufacturing plant for vacuum-packed compresses having a cooling effect comprising:
(i) a dry compress manufacturing unit comprising:
a device for longitudinally moving a water-permeable textile lower sheet which is continuously unwound and delivered flat to a delivery end of said dry compress manufacturing unit, underneath an absorbent particle powder feed hopper;
a device for depositing successive doses of said powder in grooves formed longitudinally in said moving lower sheet by reversible heat deformation;
a device for covering the moving sheet and powder with an upper sheet which is continuously unwound and delivered flat at the same time as said lower sheet to said delivery end of said dry compress manufacturing unit to form an assembly;
a device for isolating adjacent powder-filled grooves from each other transversely by longitudinally welding said upper sheet and lower sheet together along intervals between said adjacent grooves;
a device for forming successive compartments in each groove, each containing a dose of said absorbent particle powder, by welding said sheets together along transverse weld lines across the width of the moving assembly; and
a device for cutting the resulting moving assembly into successive dry compresses by moving the assembly between rollers one of which has a blade, thereby producing successive dry compresses, each containing doses of absorbent particles enclosed tight in separate grooves;
(ii) a water bag manufacturing unit comprising:
a device for bringing together and longitudinally welding two sides of a plastic sheet to form a longitudinally extending open-end tube, said weld being carried out to ensure watertight closure of the tube and resistance to subsequent handling thereof and to form a frangible area designed to give way;
a device for placing the longitudinally extending open-end tube in thermoplastic welding jaws perpendicular to the longitudinal axis of the tube and for transversely welding the tube to form a bag with a lower weld;
a device for feeding pressurised water in successive doses into the transversely welded tube to fill the bag with water;

a device for checking the filling level of the water in the tube by means of a water level probe;

a device for forming an upper transverse weld in the water-filled tube when the water level has reached a predetermined level, thus forming a closed bag to enclose the water, with the upper weld placed sufficiently below an upper level of the water in the tube to expel any excess water and ensure that no water bubbles are trapped in the bag; and a device for cutting the water filled bag from the tube to thus form successive water filled bags; and (iii) a vacuum-packed compress manufacturing unit comprising:

a device for thermoplastically forming individual receptacles in a watertight, airtight sheet which is delivered flat to said delivery end of said vacuum-packed compress manufacturing unit;

a device for depositing a water bag manufactured by the water bag manufacturing unit and a dry compress manufactured by the dry compress manufacturing unit in each receptacle, one on top of the other;

a device for covering the sheet of formed receptacles each filled with a water bag and a dry compress with a second watertight, airtight sheet which is delivered flat at the same time as said first watertight, airtight sheet to said delivery end of the vacuum-packing unit;

a device for closing edges around each filled receptacle by welding said first and second watertight, airtight sheets together, except for a rear edge of each said receptacle;

a device for successively creating a vacuum within each filled receptacle before transverse welding of the rear edge of each receptacle and complete closure of each receptacle by welding of said rear edge; and a device for cutting the filled and completely closed receptacles with a punch to obtain individual vacuum-packed compresses having a cooling effect, each containing a dry compress and a water bag.

9. The manufacturing plant according to claim 8, further comprising a device for transferring the dry compresses obtained at a delivery end of said dry compress manufacturing unit to a feeding side of said vacuum packed compress manufacturing unit, with said device for transferring being designed to also pick up each water bag at a delivery end of said bag manufacturing unit and to transfer a dry compress from said dry compress manufacturing unit and a water bag from said water bag manufacturing unit together into each pre-formed receptacle in said vacuum packed compress manufacturing unit.

10. The manufacturing plant according to claim 9, further comprising videometric inspection equipment to ensure that a dose of absorbent polymer powder is present inside each dry compress prior to transferring the dry compress with the transferring device.

11. A process for manufacturing compresses having a cooling effect and containing absorbent polymer particles, comprising:

manufacturing dry compresses wherein said particles are enclosed between a lower sheet and an upper sheet of particle retention material which are continuously delivered along a dry compress manufacturing unit in which the following operations take place, successively:

grooves are formed in said lower sheet by the application of heating pins aligned perpendicular to a direction of travel of the lower sheet, successive doses of absorbent polymer powder are deposited in said grooves over a predetermined length of said grooves after which the lower sheet is covered with said upper sheet;

the two sheets are longitudinally welded together along intervals between adjacent grooves in order to separate laterally said grooves into distinct absorbent polymer-filled compartments;

the ends of said compartments are transversely welded along a line perpendicular to the direction of travel, at either side of said predetermined length of said grooves in which there is no polymer; and then cutting along said transverse weld lines to obtain successive dry compresses.

12. The process according to claim 11, including a subsequent vacuum-packing step for said dry compresses comprising:

the lamination of two watertight, airtight films, including a lower film in which receptacles are formed by hot deformation and in which a dry compress and an associated water bag are deposited one on top of the other, with the water bag containing a pre-determined quantity of water for the activation by swelling with water of all the absorbent polymer particles contained in the compress; and the films are then welded together between the filled receptacles along longitudinal and transverse weld lines while forming a vacuum between two successive transverse weld operations to form an assembly and cutting the assembly along said longitudinal and transverse weld lines to separate the assembly into finished vacuum-packed compresses with a cooling effect.

* * * * *